(12) United States Patent
Schiffman

(10) Patent No.: US 8,071,550 B2
(45) Date of Patent: Dec. 6, 2011

(54) METHODS FOR TREATING UTERINE DISORDERS

(75) Inventor: Rhett M. Schiffman, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 2280 days.

(21) Appl. No.: 10/379,157

(22) Filed: Mar. 3, 2003

(65) Prior Publication Data

US 2004/0175399 A1    Sep. 9, 2004

(51) Int. Cl.
*A61K 38/16*    (2006.01)
(52) U.S. Cl. ...... 514/19.2; 514/1.1; 514/12.1; 514/18.1; 514/18.8; 530/300; 530/350
(58) Field of Classification Search ................ 514/2, 12, 514/1.1, 12.1, 18.1, 18.8, 19.2; 530/350, 530/300
See application file for complete search history.

(56) References Cited

U.S. PATENT DOCUMENTS

| | | | |
|---|---|---|---|
| 5,437,291 A | 8/1995 | Pasricha et al. | |
| 5,670,484 A | 9/1997 | Binder | |
| 5,714,468 A | 2/1998 | Binder | |
| 5,766,606 A | 6/1998 | Brady | |
| 5,989,545 A | 11/1999 | Foster et al. | |
| 6,063,768 A | 5/2000 | First | |
| 6,113,915 A | 9/2000 | Aoki et al. | |
| 6,139,845 A | 10/2000 | Donovan | |
| 6,143,306 A | 11/2000 | Donovan | |
| 6,261,572 B1 | 7/2001 | Donovan | |
| 6,265,379 B1 | 7/2001 | Donovan | |
| 6,306,423 B1 | 10/2001 | Donovan et al. | |
| 6,312,708 B1 | 11/2001 | Donovan | |
| 6,831,059 B2 * | 12/2004 | Donovan | 514/2 |

FOREIGN PATENT DOCUMENTS

| | | |
|---|---|---|
| DE | A 61 K 7/32 | 11/1998 |
| WO | WO 96/33273 | 10/1996 |
| WO | WO 99/03483 | 7/1998 |
| WO | WO 99/03483 | 1/1999 |
| WO | WO 99/17806 | 4/1999 |
| WO | WO 00/10598 | 3/2000 |
| WO | WO 00/15245 | 3/2000 |
| WO | WO 00/24419 | 5/2000 |
| WO | WO 00/57897 | 10/2000 |
| WO | WO 00/62746 | 10/2000 |
| WO | WO 00/74703 A2 | 12/2000 |
| WO | WO 01/21213 A2 | 3/2001 |
| WO | WO 02/74327 | 3/2002 |

OTHER PUBLICATIONS

Vilos (Minerva Ginecol. Oct. 2003; 55 (5): 417-423).*
Volpe et al. (Eur. J. Obstet. Gynecol. Reprod. Biol. May 10, 1991; 39 (3): 223-225).*
Dqani et al. (Acta Obstet. Gynecol. Scand. Jan. 1998; 77 (1): 74-77).*
Wiznitzer et al. (Biochem. Biophys. Res. Commun. May 16, 1988; 152 (3): 1326-1331).*
Sion-Vardi et al. (J. Urol. Nov. 1992; 148 (5): 1568-1570).*
Eidne et al. (J. Clin. Endocrinol. Metab. Mar. 1987; 64 (3): 425-432).*
Bramley et al. (Placenta. Oct. 1994; 15 (7): 733-745).*
Laske et al. (J. Neurosurg. Mar. 1994; 80 (3): 520-526).*
Hoffman et al. (Head Neck. Mar. 1997; 19 (2): 92-97).*
Chegini et al. (J. Clin. Endocrinol. Metab. Sep. 1996; 81 (9): 3215-3221).*
Dong et al. (Mol. Hum. Reprod. Sep. 1998; 4 (9): 893-898).*
Raga et al. (Biol. Reprod. Sep. 1998; 59 (3): 661-669).*
Koticha et al. (J. Cell Sci. Aug. 15, 2002; 115 (Pt 16): 3341-3351).*
Morris et al. (Am. J. Physiol. Heart Circ. Physiol. Dec. 2002; 283 (6): H2627-H2635).*
Vazquez-Martinez et al. (Endocrinology. Dec. 2001; 142 (12): 5364-5370).*
Chaddock et al. (Infect. Immun. May 2000; 68 (5): 2587-2593).*
Ahnert-Hilger et al. (Eur. J. Neurosci. Mar. 1998; 10 (3): 1145-1152).*
Blasi et al. (Nature. Sep. 9, 1993; 365 (6442): 160-163).*
Graham et al. (Ann. N. Y. Acad. Sci. Oct. 2002; 971: 210-221).*
Jongerius et al. (Laryngoscope. Jan. 2003; 113 (1): 107-111).*
Andrews et al. (Surg. Endosc. Aug. 1999; 13 (8):742-746).*
Quintanar et al. (Endocr. Regul. Mar. 2004; 38 (1): 1-6).*
Wilson et al. (Expert Opin. Investig. Drugs. Nov. 2007; 16 (11): 1851-1863).*
Ramakrishnappa et al. (Anim. Reprod. Sci. Aug. 2005; 88 (1-2): 95-113).*
Li et al. (Protein Eng. 2002; 15 (5): 419-427).*
Emons et al. (J. Clin. Endocrinol. Metab. Dec. 1993; 77 (6): 1458-1464).*
Anderson, Johan et al., Differential sorting of SNAP-25a and SNAP-25b proteins in neuroblastoma cells; *European Journal of Cell Biology*; 79, Nov. 2000; pp. 781-789.
Balakina, G.B. et al., *Arkh Anat Gistof Embriol*; 1986; 90(4); pp. 73-77 No Translation.
Blasl, Juan et al., Botuligum neurotoxin A selectively cleaves the synaptic protein SNAP-25; *Nature*; vol. 365; Sep. 9, 1993; pp. 160-162.
Boyd, Robert S. et al., The Effect of Botulinum Neurotoxins on the Release of Insulin from the Insulinoma Cell Lines HIT-15 and TINm5F(*); Abstract; JBC Online 270(31); 18216.
Cabello, Gertrudis et al., A Rat Mammary Tumor Model Induced by the Organophosphorous Pesticides Parathion and Malathion, Possibly through Acetycholinesterase Inhibition; *Environmental Health Perspectives*; vol. 109; No. 5; May 2001; pp. 471-479.
Coffey, Robert J. et al., Stereotactic and Diagnostic Imaging: Methods of Correlation with Traditional Stereotactic Atlases; *A Neuroimaging Atlas for Surgery of the Brain Including Radiosurgery and Stereotaxis*; Published by Lippincott—Raven, Philadelphia/New York; pp. 1-7.
Cukan, Michael C. et al., Expression of SNAP-23 and SNAP-25 in the Pancreatic Acinar Tumor Cell Line AR42J; *Molec Biol Cell*; 1999; 20(Suppl); 398a; # 2305.

(Continued)

*Primary Examiner* — Stephen Rawlings

(74) *Attorney, Agent, or Firm* — Hal Gibson; Debra Condino

(57) ABSTRACT

A method for treating uterine disorders, including hyperplasic, hypertonic, cystic and/or neoplastic uterine gland tissue by local administration of a botulinum toxin to or to the vicinity of the afflicted uterine tissue.

8 Claims, 2 Drawing Sheets

OTHER PUBLICATIONS

Dayanithi, G. et al., Release of Vasopressin From Isolated Permeabilized Neurosecretory Nerve Terminals is Blocked by the Light Chain of Botulinum A Toxin; *Neuroscience*; 1990; 39(3) pp. 711-715.

Der, Roger et al., Gastric Neoplasms; Gastrointestinal Pathology; by Parakrama Chandrasoma, MD, MRCP (UK); pp. 105-144.

Doggweiler, R. et al., Botulinum Toxin Type A Causes Diffuse and Highly Selective Atrophy of Rat Prostate; *J. Urol*; 157(4) Suppl. Abstr 666, 1997 p. 363.

Dorosevich, A.E. et al., *Arkh Patol*; 1994; 56(6); pp. 49-53.

Duggan, Michael J. et al., A survey of botulinum neurotoxin substrate expression in cells; *Mov Disord*; May 1995; 10(3) p. 376.

Ellis, I.O. et al., Tumors of the breast; *Diagnostic Histopathology of Tumors* vol. 1 edited by Christopher D.M. Fletcher; pp. 865-930.

Fabian, Carol J. et al., Beyond Tamoxifen New Endpoints for Breast Cancer Chemoprevention, New Drugs for Breast Cancer Prevention; *Annals N Y Academy of Sciences*; 2001; 952; pp. 44-59.

Goodall, Anna R. et al., Occurrence of Two Types of Secretory Vesicles in the Human Neuroblastoma SH-SY5Y; *Journal of Neurochemistry*; vol. 68, No. 4, 1997, pp. 1542-1552.

Graff, Lothar et al., Expression of Vesicular Monoamine Transporters, Synaptosomal-associated Protein 25 and Syntaxin1; *Cancer Research*; 61 (5); 2138 Abstract.

Grosse, J. et al., Synaptosome-Associated Protein of 25 Kilodaltons in Oocytes and Steroid-Producing Cells of Rat and Human Ovary: Molecular Analysis and Regulation by Gonadotropins; *Biology of Reproduction*; 63, 2000; pp. 643-650.

Hohne-Zell, Barbara et al., Functional Importance of Synaptobrevin and SNAP-25 during Exocytosis of Histamine by Rat Gastric Enterochromaffin-Like Cells; *ENDO*; 1997; vol. 138, No. 12; pp. 5518-5526.

Huang, X., et al., Truncated SNAP-25 (1-197), like botulinum neurotoxin A, can inhibit insul secretion from HIT-T15 insulinoma cells, *Molecular Endocrinology*, 12(7):1060-1070.

Lawrence, G.W., et al., Distinct exocytotic responses of intact and permeabilised chromaffin cells after cleavage of the 25-kDa synaptosomal-assocated protein (SNAP-25) or synaptobrevin by botulinum toxin A or B, *Eur J.Biochem*, Mar. 15, 1996;236(3):877-86.

Lidbeck, J, Central hyperexcitability in chronic musculoskeletal pain: a conceptual breakthrough with multiple clinical implications, *Pain Res Manage*, vol. 7 No. 2 Summer 2002, pp. 81-92.

Maksymowych, A.B., et al., Binding and transcytosis of botulinum neurotoxin by polarized human colon carcinoma cells, *J Biol Chem* Aug. 1998 273(34):21950-21957.

Meyer, K.E., A comparative systemic toxicity study of neurobloc in adult and juvenile cynomolgus monkeys, *Mov Disord* 2000;15(suppl 2):54.

Morlin, B., et al., Does nitric oxide act as a cellular messenger in muscarinic endometrial secretion in the guinea-pig?, *Acta Physiol Scand*, 2002, 174, 311-315.

Morris, J.L., Botulinum neurotoxin A attenuates release of norepinephrine but not NPY from vasoconstrictor neurons, *Am J Physiol Heart Circ Physiol*, Dec. 2002; 283(6):H2627-35.

Oyler, G.A., Distribution and expression of SNAP-25 immunoreactivity in rat brain, rat PC-12 cells and human SMS-KCNR neuroblastoma cells, *Developmental Brain Research*, 65 (1992) 133-146.

Panagiotou, S., et al., Opioid agonists modify breast cancer cell proliferation by blocking cells to the $G_2/M$ phase of the cycle: involvement of cytoskeletal elements, *Journal of Cellular Biochemistry*, 73:204-211 (1999).

Pesic, S., et al., Acetylcholine-induced contractions in the porcine internal mammary artery: possible role of muscarinic receptors, *J. Vet Med A* 46, 509-515 (1999).

Sadoul, K., et al., SNAP-25 is expressed in islets of langerhans and is involved in insulin release, *The Journal of Cell Biology*, vol. 128, 1995, 1019-1028.

Seneviraine, S., Botox and the management of pectoral spasm after subpectoral implant insertion, *Plast Reconstr Surg*, Jul. 2000;106(1):224-225.

Shukla, A., et al., SNAP-25 associated Hrs-2 protein colocalizes with AQP2 in rat kidney collecting duct principal cells, *Am J Physiol Renal Physiol*, 281:F546-F556, 2001.

Sivridis, E., et al., Prognostic aspects on endometrial hyperplasia and neoplasis, *Virchows Arch* (2001) 439:118-126.

Sunaga, H., et al., Expression of Granulocyte Colony-stimulating factor receptor and platelet-derived endothelial cell growth factor in oral and oropharyngeal precancerous lesions, *Anticancer Research*, 21:2901-2906 (2001).

Van Poppel, H., et al., Precancerous Lesions in the Kidney, *Scand J Urol Nephrol Suppl* 205: 136-165, 2000.

Zimmerman, U., et al., Proteolysis of synaptobrevin, syntaxin, and SNAP-25 in alveolar epithelial type II cells, *IUBMB Life*, 48:453-458, 1999.

Verheyden, Jean et al., Other Noncosmetic Uses of Botox, Seminars in Cutaneous Medicine and Surgery, vol. 20, No. 2 Jun. 2001; pp. 121-126.

Johnson, Eric A., *Clostridial Toxins as Therapeutic Agents: Benefits of Nature's Most Toxic Proteins*, Annu. Rev. Microbiol. 1999, 53; pp. 551-575.

*Harrison's Principles of Internal Medicine* 14th Edition by Fauci et al.; Published by McGraw-Hill, cover & publication information.

Majo, G., et al., Immunocytochemical analysis of the synaptic proteins SNAP-25 and Rab3A in human pituitary adenomas. Overexpression of SNAP-25 in the mammosomatotroph lineages, *J Pathol*. Dec. 1997;183(4):440-6.

Garza, et al., *Clostridium Botulinum Toxin Inhibits Myometrial Activity in vitro: Possible Application on the Prevention of Preterm Labor After Fetal Surgery*, J Pediatr Surg Mar. 2003 38(3), pp. 511-513.

* cited by examiner

METHODS FOR TREATING UTERINE DISORDERS

BACKGROUND

The present invention relates to methods for treating uterine disorders. In particular, the present invention relates to methods for treating uterine glandular disorders with a botulinum toxin.

An object of the present invention is to treat uterine tissues, including atypical uterine tissues, such as hyperplasic tissues, fibroids and uterine neoplasms (including tumors and cancers). A further object of the present invention is to prevent the development of, or to cause the regression or remission of, atypical uterine tissues, fibroids and neoplasms. An additional object of the present invention is to treat uterine disorders, both benign and cancerous, as well as for treating hyperplasic and/or hypertonic uterine gland cells by local administration of a Clostridial toxin to or to the vicinity of the afflicted uterine tissue.

Uterine Disorders

The uterus is a hollow muscular organ with significant glandular tissue. Upon release from the ovaries an egg travels through the Fallopian tubes to the uterus and if fertilized, the ovum embeds in the endometrium, a glandular lining of the uterus. The cervical canal extends from the vagina through the cervix (the lower portion of the uterus) to the body of the uterus. The fundus is the top of the uterus (the area between the fallopian tubes). The myometrium is the muscular wall of the uterus.

It is known that hyperplasic uterine tissues can, if not treated, develop into cancerous tissue. See e.g. Sivridis E. et al., *Prognostic aspects on endometrial hyperplasia and neoplasia*,
Virchows Arch 2001 August; 439(2):118-26. Additionally it is known that: different hyperplasia, metaplasic or atypical breast tissues can develop into cancers (see e.g. Ellis I. O., et al, *Tumors of the Breast*, chapter 16 (pages 865-930) of "Diagnostic Histopathology of Tumors", volume 1, edited by Fletcher C. D. M., second edition, Churchill Livingstone (2000), discussed further infra, as well as Fabian C. J. et al *Beyond tamoxifen new endpoints for breast cancer chemoprevention, new drugs for breast cancer prevention*. Ann NY Acad Sci 2001 December; 952:44-59); hyperplasic intestinal tissues, such as polyps can transform into carcinomas (see e.g. Der, R. et al *Gastric Neoplasms*, chapter 5 (pages 105-144) of Chandraspma, P., "Gastrointestinal Pathology", Appleton & Lange (1999), in particular pages 106-107; oral and oropharyngeal epithelial hyperplasia indicates a precancerous lesion. Sunaga H., et al. *Expression of granulocyte colony-stimulating factor receptor and platelet-derived endothelial cell growth factor in oral and oropharyngeal precancerous lesions*. Anticancer Res 2001 July-August; 21 (4B):2901-6, and; kidney and prostate cell hyperplasia has been documented as a factor leading to development of cancerous cells. Van Poppel, H., et al., *Precancerous lesions in the kidney* Scand J Urol Nephrol Suppl 2000; (205): 136-65.

Common cancers of the uterus include cervical and endometrial cancer. Endometrial cancer occurs most often in woman between the ages of 50 and 70 and it more common in women who have not had children. The usual symptom of endometrial cancer is vaginal bleeding after menopause. Diagnosis can be by biopsy or endometrial scraping.

Cervical cancer can take many years to develop. Before it does, early changes can occur in the cells of the cervix. The abnormal, non-cancerous cells (but which may become cancerous) are called cervical intra-epithelial neoplasia (CIN) or dyskaryosis.

Smooth muscle tumors of the uterus can be submucosal, intramural, and subserosal leiomyomata (fibroids). Uterine leiomyomas (fibroids) of the uterus are one of the most common pathologic abnormalities of the female genital tract. Fibroids are typically mostly in the muscle of the uterus (intramural) and by virtue of their size or position can impinge upon the endometrium and cause bleeding. Fibroids of the uterus are present in about 25% of women and require treatment: (a) if due to position or size they cause irregular uterine bleeding that cannot be controlled with hormonal therapy or removal of a polyp-like fibroid (submucosal) from the inside of the uterus at time of hysteroscopy & D&C; (b) they are so big (usually softball size or larger) that they give either pelvic pressure, bladder or rectal pressure or pelvic fullness symptoms; (c) they are in a position (usually near the ovaries or they have grown so rapidly that there is a question they might be malignant; (d) they cause recurrent pain due to the blood supply being compromised; (e) the fibroids cause distortion of the endometrial cavity and women have problems either during pregnancy or then they have frequent miscarriages.

The location of fibroids is variable. Most commonly, they are intramural and are noted by an irregular enlargement of the uterine corpus. The tumors can enlarge from the surface of the uterus late or early in their course and become subserous. Alternatively, they can protrude into the endometrial cavity and distort it. The submucous fibroid is one that has penetrated the endometrial cavity and has enlarged so as to stretch the mucosa over the tumor to the point that the submucosa is absent and ulceration of the overlapping endometrium may occur. Although not all submucous fibroids cause clinical bleeding or interfere with conception and normal pregnancy, they certainly are associated with significant symptomatic disturbances of this type, exhibiting menorrhagia, anemia, pelvic cramping, infection, infertility, and abortion among the more commonly seen problems.

Myomectomy removes the fibroid without removing the uterus. Laparoscopic Myomectomy involves removing pedunculated subserosal fibroids through the navel and abdomen with the use of a laparoscope. Hysteroscopic Myomectomy involves the vaginal removal of submucosal fibroids through the use of a hysteroscope. Laparotomy (abdominal myomectomy) involves an abdominal incision that allows for the removal of all fibroids no matter their location, size, or number. Laparoscopic myomectomy with allows for the removal of slightly larger subserosal fibroids than what the laparoscope alone can handle and generally includes a relatively small incision of 3 inches or less in the abdomen.

Laparoscopic assisted vaginal myomectomy (LAVM) allows for the laparoscopic removal of subserosal fibroids from the uterus with the total removal of fibroid material through a vaginal incision. Uterine fibroid embolization (UFE, also known as uterine artery embolization UAE) is a minimally-invasive, non-surgical procedure performed by an interventional radiologist (IR). This procedure involves placing a catheter into the artery and guiding it to the uterus. Small particles are then injected into the artery. The particles block the blood supply feeding the fibroids.

Myolysis involves surgical instruments that are inserted through a laparoscopic incision in the abdomen and a high frequency electrical current that is sent to the fibroid. The electrical current causes the blood vessels to vaso-constrict (become very small or close down) and this basically cuts off the blood flow to the fibroids. The fibroids remain in place and are not surgically removed. Without a blood supply, the fibroids eventually die and shrink.

There are three primary forms of hysterectomy. Subtotal, total and radical hysterectomy. Subtotal Hysterectomy involves only the removal of the uterus. The pelvic structural ligaments are not cut and the cervix is left in place. Fallopian tubes and ovaries may or may not be removed. This procedure is always done through the abdomen.

Total Hysterectomy involves removing both the body of the uterus and the cervix, which is the lower part of the uterus. It can sometimes be done through the vagina (vaginal hysterectomy); at other times, a surgical incision in the abdomen is preferable. In a total hysterectomy and bilateral salpingo-oophorectomy, the ovaries and fallopian tubes are removed, along with the uterus and cervix.

In radical hysterectomy the entire uterus and usually both tubes and ovaries as well as the pelvic lymph nodes are removed through the abdomen.

In addition to the direct surgical risks, there may be longer-term physical and psychological effects, potentially including depression and loss of sexual pleasure. If the ovaries are removed along with the uterus prior to menopause, there is an increased risk of osteoporosis and heart disease as well.

The surgical risks of hysterectomy and myomectomy include fever, bladder infection and wound infection. A blood transfusion before surgery may be necessary because of anemia or during surgery for blood loss. Complications related to anesthesia may occur. Other complications can include blood clots, postoperative hemorrhage, bowel obstruction, injury to the urinary tract and death (eleven women die for every 10,000 hysterectomies performed).

Since clinically undetectable uterine cancer cells may be left following local excision of the cancer, typically radiation therapy is given for local tumor control. Radiation therapy can also be used preoperatively to shrink large uterine tumors and make them more easily resectable. Palliative radiation therapy is commonly used to relieve the pain of bone metastasis and for the symptomatic management of metastases to other sites, such as the brain. Fatigue, skin reactions, changes in sensation, color and texture of the skin, and uterine swelling are common during and immediately following a course of radiation therapy to the uterus.

Chemotherapy, hormone therapy, or a combination of the two can be used to palliate the effects of metastatic uterine disease. Recommendations for adjuvant chemotherapy and/or adjuvant hormone therapy are usually based on the number of positive axillary nodes, menopausal status, size of the primary tumor, and the estrogen receptor assay. The chemotherapeutic drugs most commonly used are alkylating agents, antimetabolites, antitumor antibiotics (Herceptin) and vinca alkaloids. Hormone manipulation is achieved primarily through hormone blockers and infrequently by surgical removal of sex hormone-producing glands (oophorectomy, adrenalectomy, or hypophysectomy). Tamoxifen, an anti-estrogen, is the most widely used hormonal agent. The second-line hormonal agents, such as Femara, and Arimidex, are now available for ER/PR negative patients and/or patients who failed tamoxifen. Unfortunately, chemotherapy for uterine cancer can have numerous deleterious side effects including fatigue, weight gain, nausea, vomiting, alopecia, disturbances in appetite and taste, neuropathies, diarrhea, bone marrow suppression, menopausal symptoms, hair loss and weight gain. Additionally, the first line drug of choice, tamoxifen, can increase the risk of uterine cancer and blood clots.

Botulinum Toxin

The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of botulinum toxin (purified neurotoxin complex) type A[1] is a $LD_{50}$ in mice. One unit (U) of botulinum toxin is defined as the $LD_{50}$ upon intraperitoneal injection into female Swiss Webster mice weighing 18-20 grams each. Seven immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Botulinum toxin apparently binds with high affinity to cholinergic motor neurons, is translocated into the neuron and blocks the release of acetylcholine.

[1] Available from Allergan, Inc., of Irvine, Calif. under the tradename BOTOX®.

Botulinum toxins have been used in clinical settings for the treatment of neuromuscular disorders characterized by hyperactive skeletal muscles. Botulinum toxin type A has been approved by the U.S. Food and Drug Administration for the treatment of blepharospasm, strabismus, hemifacial spasm and cervical dystonia. Non-type A botulinum toxin serotypes apparently have a lower potency and/or a shorter duration of activity as compared to botulinum toxin type A Clinical effects of peripheral intramuscular botulinum toxin type A are usually seen within one week of injection. The typical duration of symptomatic relief from a single intramuscular injection of botulinum toxin type A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

It has been reported that botulinum toxin type A has been used in clinical settings as follows:
  (1) about 75-250 units of BOTOX® per intramuscular injection (multiple muscles) to treat cervical dystonia;
  (2) 5-10 units of BOTOX® per intramuscular injection to treat glabellar lines (brow furrows) (5 units injected intramuscularly into the procerus muscle and 10 units injected intramuscularly into each corrugator supercilii muscle);
  (3) about 30-80 units of BOTOX® to treat constipation by intrasphincter injection of the puborectalis muscle;
  (4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
  (5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).
  (6) to treat upper limb spasticity following stroke by intramuscular injections of BOTOX® into five different upper limb flexor muscles, as follows:
    (a) flexor digitorum profundus: 7.5 U to 30 U
    (b) flexor digitorum sublimus: 7.5 U to 30 U
    (c) flexor carpi ulnaris: 10 U to 40 U
    (d) flexor carpi radialis: 15 U to 60 U
    (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

The success of botulinum toxin type A to treat a variety of clinical conditions has led to interest in other botulinum toxin serotypes. A study of two commercially available botulinum type A preparations (BOTOX® and Dysport®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX® and Dysport®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety. Furthermore, in rabbits, type B was more antigenic than as BOTOX®, possibly because of the higher protein load injected to achieve an effective dose of botulinum toxin type B.

It is known to use a botulinum toxin to treat: intrathecal pain (see e.g. U.S. Pat. No. 6,113,915); paragangliomas (see e.g. U.S. Pat. No. 6,139,845); otic disorders (see e.g. U.S. Pat. No. 6,265,379); pancreatic disorders (see e.g. U.S. Pat. Nos. 6,143,306 and 6,261,572); migraine (see e.g. U.S. Pat. No. 5,714,468); smooth muscle disorders (see e.g. U.S. Pat. No. 5,437,291); prostate disorders, including prostatic hyperplasia (see e.g. WO 99/03483 and Doggweiler R., et al *Botulinum toxin type A causes diffuse and highly selective atrophy of rat prostate*, Neurourol Urodyn 1998; 17(4):363); autonomic nerve disorders, including hyperplasic sweat glands (see e.g. U.S. Pat. No. 5,766,606); wound healing (see e.g. WO 00/24419); reduced hair loss (see e.g. WO 00/62746); skin lesions (see e.g. U.S. Pat. No. 5,670,484), and; neurogenic inflammatory disorders (see e.g. U.S. Pat. No. 6,063,768). U.S. Pat. No. 6,063,768 cursorily discloses at column 6 lines 39-42 treatment of the inflammatory joint condition pigmented villonodular synovitis and a particular type of joint cancer, synovial cell sarcoma. Column 6, line 53 of U.S. Pat. No. 6,063,768 also discloses, without further explanation, that "tumors" can be treated.

Additionally it has been disclosed that targeted botulinum toxins (i.e. with a non-native binding moiety) can be used to treat various conditions (see e.g. U.S. Pat. No 5,989,545, as well as WO 96/33273; WO 99/17806; WO 98/07864; WO 00/57897; WO 01/21213; WO 00/10598.

A botulinum toxin has been injected into the pectoral muscle to control pectoral spasm. See e.g. Senior M., *Botox and the management of pectoral spasm after subpectoral implant insertion*, Plastic and Recon Surg, July 2000, 224-225.

Both liquid stable formulations and pure botulinum toxin formulations have been disclosed (see e.g. WO 00/15245 and WO 74703) as well as topical application of a botulinum toxin (see e.g. DE 198 52 981).

Acetylcholine

Typically or in general, only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system secrete the neurotransmitter norepinephine. In most instances acetylcholine has an excitatory effect. However, acetylcholine is known to have inhibitory effects at some of the peripheral parasympathetic nerve endings, such as inhibition of the heart by the vagus nerves.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

Wide Distribution of the Botulinum Toxin Substrate

It is known that a botulinum toxin can denervate muscle cells resulting in a flaccid paralysis due to a presynaptic inhibition of acetylcholine release from neurons at a neuromuscular junction. The proteolytic domain of a botulinum toxins acts upon a particular substrate in the cytosol of target cells, cleavage of the substrate preventing membrane docking and exocytosis of acetylcholine containing secretory vesicles. The absence of acetylcholine in the synaptic cleft between innervating neuron and muscle cell prevents stimulation of the muscle cells and paralysis thereby results.

The botulinum toxins are intracellular proteases that act specifically on one or more of three different proteins which control the docking of acetylcholine to containing secretory vesicles. These specific substrates for the botulinum toxins are synaptobrevin, syntaxin and/or SNAP-25. See e.g. Duggan M. J., et al., *A survey of botulinum neurotoxin substrate expression in cells*, Mov Disorder 10(3); 376:1995, and Blasi J., et al., *Botulinum neurotoxin A selectively cleaves the synaptic protein SNAP-25*. Nature 365; 160-163:1993. For botulinum toxin types B, D, F and G the particular intracellular substrate is synaptobrevin. SNAP-25, synaptobrevin and syntaxin are known as SNAREs (soluble N-ethylmaleimide sensitive factor attachment protein receptors).

Significantly, it is not only the nerves which innervate muscles which contain the substrate for the botulinum toxins: "The presence of SNAP-25 in presynaptic regions of numerous neuronal subsets and in neural crest cell lines suggests that this protein subserves an important function in neuronal tissues." Oyler G. A. et al., *Distribution and expression of*

*SNAP-25 immunoreactivity in rat brain, rat PC-12 cells and human SMS-KCNR neuroblastoma cells*, Brain Res Dev Brain Res 1992 Feb. 21; 65(2):133-146, 1992.

Additionally, "[T]he wide occurrence of the SNARE proteins in endocrine cells suggests that they may also serve as general diagnostic markers for endocrine tumors . . . ", Graff, L., et al. *Expression of vesicular monoamine transporters, synaptosomal-associated protein 25 and syntaxin1: a signature of human small cell lung carcinoma*, Cancer Research 61, 2138-2144, Mar. 1, 2001, at page 2138. For example, it is known that SNAP-25 is widely distributed in neuroendocrine cells (including in chromaffin cells, PC12, GH3, and insulinomas). Furthermore, the botulinum toxin substrate synaptobrevin has been found in fibroblasts and myeloid cells (e.g. mast cells). Duggan M., et al., supra.

Indeed, SNAREs apparently influence or control the membrane fusion of secretory vesicles in most if not all secretory cells. Andersson J., et al, *Differential sorting of SNAP-25a and SNAP-25b proteins in neuroblastoma cells*, Eur J. Cell Bio 79, 781-789:November 2000.

Thus, the substrate for a botulinum toxin are not restricted to neuronal cells which release the neurotransmitter acetylcholine. The botulinum toxin substrates are therefore "ubiquitously involved in membrane-membrane fusion events" and the evidence points to "a universal mechanism for membrane fusion events" (i.e. for the docking of secretory vesicles with the cell wall) (Duggan 1995, supra).

Thus, the intracellular substrate for botulinum toxin has a ubiquitous distribution in both neuronal and non-neuronal secretory cells. This is clearly illustrated by discovery of the presence of SNAP-25 (a 25 kiloDalton synaptosomal-associated protein and substrate for at least botulinum toxin type A) in at least:

(1) the pancreas (Sadoul K., et al., *SNAP-25 is expressed in islets of Langerhans and is involved in insulin release*, J. Cell Biology 128; 1019-1029:1995;

(2) the hypophysis (Dayanithi G., et al. *Release of vasopressin from isolated permeabilized neurosecretory nerve terminals is blocked by the light chain of botulinum A toxin*, Neuroscience 1990; 39(3):711-5);

(3) the adrenal medulla (Lawrence G., et al. *Distinct exocytotic responses of intact and permeabilised chromaffin cells after cleavage of the* 25-*kDa synaptosomal associated protein* (*SNAP*-25) *or synaptobrevin by botulinum toxin A or B*, Eur J. Biochem 236; 877-886:1996);

(4) gastric cells (Hohne-Zell B., et al., *Functional importance of synaptobrevin and SNAP-25 during exocytosis of histamine by rat gastric enterochromaffin*-like cells, Endocrinology 138; 5518-5526:1997;

(5) lung tumors (Graff, L., et al. *Expression of vesicular monoamine transporters, synaptosomal-associated protein* 25 *and syntaxin* 1: *a signature of human small cell lung carcinoma*, Cancer Research 61, 2138-2144, Mar. 1, 2001 (small cell lung carcinomas (SCLCs) contain SNAP-25);

(6) intestinal tumors, Maksymowych A., et al., *Binding and transcytosis of botulinum neurotoxin by polarized human colon carcinoma cells*, J of Bio. Chem, 273 (34); 21950-21957: 1998 (botulinum toxin is internalized by human colon cancer cells);

(7) pancreatic tumors, Huang, X., et al., Truncated SNAP-25 (1-197), like botulinum neurotoxin A, can inhibit insulin secretion from HIT-T15 insulinoma cells, Mol. Endo. 12(7); 1060-1070:1998 (" . . . functional SNAP-25 proteins are required for insulin secretion . . . ", ibid. at page 1060). See also Boyd R., et al., *The effect of botulinum neurotoxins on the release of insulin from the insulinoma cell lines HIT*-15 *and RINm5F*, J. Bio Chem. 270(31); 18216-18218: 1995, and; Cukan M., et al., *Expression of SNAP-23 and SNAP-25 in the pancreatic acinar tumor cell line AR42J*, Molec Biol Cell 20 (suppl); 398*a*, no. 2305:1999 ("SNAP-25 is a SNARE protein that mediates exocytotic events in neuronal and endocrine systems.");

(8) pituitary tumors as well as in normal pituitary cells, Majo G., et al., *Immunocytochemical analysis of the synaptic proteins SNAP-25 and Rab3A in human pituitary adenomas. Overexpression of SNAP-25 in the mammososmatotroph lineages, J. Pathol* 1997 *December;* 183(4): 440-446;

(9) neuroblastomas, Goodall, A., et al., *Occurrence of two types of secretory vesicles in the human neuroblastoma SH-SY5Y*, J. of Neurochem 68; 1542-1552:1997. See also Oyler, G. A, *Distribution and expression of SNAP-25 immunoreactivity in rat brain, rat PC-12 cells and human SMS—KCNR neuroblastoma cells*, Dev. Brain Res. 65 (1992); 133-146. Note that Goodall (1992) discusses only in vitro identification of certain vesicle docking proteins in a single neuroblastoma cell line;

(10) kidney cells (Shukla A., et al., *SNAP-25 associated Hrs-2 protein colocalizes with AQP2 in rat kidney collecting duct principal cells*, Am J Physiol Renal Physiol 2001 September; 281 (3):F546-56 (SNAP-25 is involved in kidney cell "regulated exocytosis"), and;

(11) normal lung cells (Zimmerman U. J., et al., *Proteolysis of synaptobrevin, syntaxin, and SNAP-25 in alveolar epithelial type II cells*, IUBMB Life 1999 October; 48(4): 453-8), and; (12) all ovarian cells (Grosse J., et al., *Synaptosome associated protein of* 25 *kilodaltons in oocytes and steroid producing cells of rat and human ovary: molecular analysis and regulation by gonadotropins*, Biol Reprod 2000 August; 63(2): 643-50 (SNAP-25 found "in all oocytes and in steroidogenic cells, including granulosa cells (GC) of large antral follicles and luteal cells".

Cholinergic Mammary Gland Tissues

Diverse hyperplasic and neoplastic mammary gland cells are influenced by cholinergic mechanisms. Thus, it has been discovered that there is a "cholinergic mechanism in the alveolar cells activity". Balakina G. B., et al., *Localization of choline acetyltransferase in the alveolar portion of the mammary gland of the white mouse*, Arkh Anat Gistol Embriol 1986 April; 90(4):73-7. Additionally, there is cholinergic influence upon both mammary dysplasia (fibrocysts) and mammary carcinoma tissues (Dorosevichi A. E., et al., *Autonomic nerve endings and their cell microenvironment as one of the integral parts of the stromal component in breast dysplasia and cancer*, Arkh Patol 1994 November-December; 56(6):49-53), as well as "a direct cholinergic stimulation of smooth muscle cells" in mammary arteries (Pesic S., et al., *Acetylcholine-induced contractions in the porcine internal mammary artery; possible role of muscarinic receptors*, Zentralbl Veterinarmed A 1999 October; 46(8): 509-15).

Significantly, an increase in acetylcholine due to inhibition of cholinesterase has been implicated in increase mammary cell proliferation followed by the development of mammary carcinomas. Cabello G., et al, *A rat mammary tumor model induced by the organophosphorous pesticides parathion and malathion, possibly through acetylcholinesterase inhibition*, Environ Health Perspect 2001 May; 109(5):471-9. Thus, a decrease in breast cancer cell proliferation appears to be mediated by a cholinergic mechanism. Panagiotou S., "*Opioid agonists modify breast cancer cell proliferation by blocking cells to the G2/M phase of the cycle: involvement of cytoskeletal elements*, J Cell Biochem 1999 May 1; 73(2): 204-11.

Adrenal Medulla

The adrenal or suprarenal glands are small, triangular-shaped structures located on top of the kidneys. Each adrenal gland comprises an adrenal cortex or outer portion and an adrenal medulla or inner portion. The cortex surrounds and encloses the medulla.

The adrenal cortex secretes the hormones cortisol and aldosterone. Cortisol is produced during times of stress, regulates sugar usage, and is essential for maintenance of normal blood pressure. Aldosterone is one of the main regulators of salt, potassium and water balance. If both adrenal glands are removed cortisol and aldosterone replacement therapy is mandatory.

The adrenal medulla secretes the catecholamines adrenalin (synonymously epinephrine) and noradrenalin (synonymously norepinephrine). These hormones are important for the normal regulation of a variety of bodily functions, including stress reaction, when they cause an increase in blood pressure, the pumping ability of the heart, and the level of blood sugar. Removal of the adrenal medulla results in little or no hormonal deficiency because other glands in the body can compensate. Contrarily, excessive catecholamine production can be life threatening.

In the normal adult male about 85% of total catecholamine made by the adrenal medulla is adrenaline, with the remaining 15% being noradrenalin. There is about 1.6 mg of catecholamine present per gram of medulla tissue. Most of the noradrenalin found in blood and urine comes not from the adrenal medulla but from postganglionic sympathetic nerve endings. If the freshly sectioned adrenal gland is placed in fixatives that contain potassium dichromate, the medulla turns brown and this is referred to as the chromaffin reaction, so named to suggest the affinity of adrenal medulla tissue for chromium salts. Hence, cells of the adrenal medulla are often called chromaffin cells. Chromaffin cells also exists outside the adrenal medulla, but usually secrete only noradrenalin, not adrenaline.

The adrenal medulla can be viewed as a sympathetic ganglion innervated by preganglionic cholinergic nerve fibers. These nerve fibers release acetylcholine which causes secretion of catecholamines (primarily adrenaline) by a process of exocytosis from the chromaffin cells of the adrenal medulla. The normal adrenal medulla is innervated by the splanchnic nerve, a preganglionic, cholinergic branch of the sympathetic nervous system. The activity of the adrenal medulla is almost entirely under such cholinergic nervous control.

Chromaffin Cell Tumors

Chromaffin cells (including the chromaffin cells of the adrenal medulla) and sympathetic ganglion cells have much in common as they are both derived from a common embryonic ancestor, the sympathagonium of the neural crest, as shown diagrammatically below. Examples of the types of neoplasms which can arise from each these cell types is shown in brackets. Each of the cell types shown can potentially secrete catecholamines.

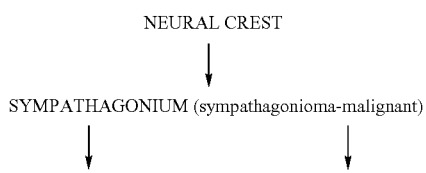

NEURAL CREST
↓
SYMPATHAGONIUM (sympathagonioma-malignant)
↓         ↓

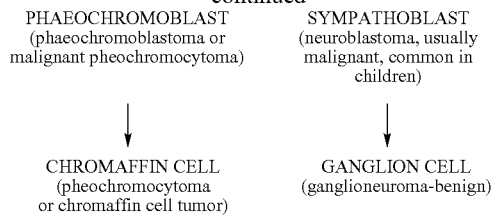

PHAEOCHROMOBLAST (phaeochromoblastoma or malignant pheochromocytoma)     SYMPATHOBLAST (neuroblastoma, usually malignant, common in children)
↓         ↓
CHROMAFFIN CELL (pheochromocytoma or chromaffin cell tumor)     GANGLION CELL (ganglioneuroma-benign)

While most chromaffin cell neoplasms occur in the adrenal medulla, ectopic and multiple location chromaffin cell tumors are known, occurring most commonly in children.

1. Paragangliomas

A paraganglia (synonymously, chromaffin body) can be found in the heart, near the aorta, in the kidney, liver, gonads, and other places and is comprised of chromaffin cells which apparently originate from neural crest cells and which have migrated to a close association with autonomic nervous system ganglion cells. A paraganglioma is a neoplasm comprised of chromaffin cells derived from a paraganglia. A carotid body paraganglioma is referred to as a carotid paraganglioma, while an adrenal medulla paraganglioma is called a pheochromocytoma or a chromaffinoma.

The carotid body is often observed as a round, reddish-brown to tan structure found in the adventitia of the common carotid artery. It can be located on the posteromedial wall of the vessel at its bifurcation and is attached by ayer's ligament through which the feeding vessels run primarily from the external carotid. A normal carotid body measures 3-5 mm in diameter. Afferent innervation appears to be provided through the glossopharyngeal nerve (the ninth cranial nerve). The glossopharyngeal nerve supplies motor fibers to the stylopharyngeus, parasympathetic secretomotor fibers to the parotid gland and sensory fibers to inter alia the tympanic cavity, interior surface of the soft palate and tonsils). Histologically, the carotid body includes Type I (chief) cells with copious cytoplasm and large round or oval nuclei. The cytoplasm contains dense core granules that apparently store and release catecholamines. The normal carotid body is responsible for detecting changes in the composition of arterial blood.

Carotid paragangliomas are rare tumors overall but are the most common form of head and neck paraganglioma. The treatment of choice for most carotid body paragangliomas is surgical excision. However, because of their location in close approximation to important vessels and nerves, there is a very real risk of morbidity (mainly cranial nerve X-XII deficits and vascular injuries) and mortality which is estimated as 3-9%. Tumor size is important because those greater than 5 cm in diameter have a markedly higher incidence of complications. Perioperative alpha and beta adrenergic blockers are given (if the carotid paraganglioma is secreting catecholamines) or less preferably angiographic embolization preoperatively. Radiotherapy, either alone or in conjunction with surgery, is a second consideration and an area of some controversy. Unfortunately, due to location and/or size, paragangliomas, including carotid paragangliomas can be inoperable.

2. Pheochromocytomas

Pheochromocytomas occur in the adrenal medulla and cause clinical symptoms related to excess catecholamine production, including sudden high blood pressure (hypertension), headache, tachycardia, excessive sweating while at rest, the development of symptoms after suddenly rising from a bent-over position, and anxiety attacks. Abdominal imaging and 24 hour urine collection for catecholamines are usually sufficient for diagnosis. Catecholamine blockade with phenoxybenzamine and metyrosine generally ameliorates symptoms and is necessary to prevent hypertensive crisis during surgery, the current therapy of choice. Standard treatment is laparoscopic adrenalectomy, although partial adrenalectomy is often used for familial forms of pheochromocytoma. Malignant (cancerous) pheochromocytomas are rare tumors.

Pheochromocytomas have been estimated to be present in approximately 0.3% of patients undergoing evaluation for secondary causes of hypertension. Pheochromocytomas can be fatal if not diagnosed or if managed inappropriately. Autopsy series suggest that many pheochromocytomas are not clinically suspected and that the undiagnosed tumor is clearly associated with morbid consequences.

The progression of changes in the adrenal medulla can be from normal adrenal medulla to adrenal medullary hyperplasia (a generalized increase in the number of cells and size of the adrenal medulla without the specific development of a tumor) to a tumor of the adrenal medulla (pheochromocytoma).

Treatment of a pheochromocytoma is surgical removal of one or both adrenal glands. Whether it is necessary to remove both adrenal glands will depend upon the extent of the disease. Patients who have had both adrenal glands removed must take daily cortisol and aldosterone replacement. Cortisol is replaced by either hydrocortisone, cortisone or prednisone and must be taken daily. Aldosterone is replaced by oral daily fludrocortisone (FLORINEF™). Increased amounts of replacement hydrocortisone or prednisone are required by such patients during periods of stress, including fever, cold, influenza, surgical procedure or anesthesia.

3. Glomus Tumors

Glomus tumors (a type of paraganglioma) are generally benign neoplasms, also arising from neuroectodermal tissues, found in various parts of the body. Glomus tumors are the most common benign tumors that arise within the temporal bone and fewer than five per cent of them become malignant and metastasize. Glomus tumors arise from glomus bodies distributed along parasympathetic nerves in the skull base, thorax and neck. There are typically three glomus bodies in each ear. The glomus bodies are usually found accompanying Jacobsen's (CN IX) or Arnold's (CN X) nerve or in the adventitia of the jugular bulb. However, the physical location is usually the mucosa of the promontory (glomus tympanicums), or the jugular bulb (glomus jugulare).

The incidence of glomus jugulare tumors is about 1:1,300,000 population and the most striking bit of epidemiology is the predominant incidence in females with the female:male incidence ratio being at least 4:1. Catecholamine secreting (i.e. functional) tumors occur in about 1% to 3% of cases.

Glomus tumors have the potential to secrete catecholamines, similar to the adrenal medulla which also arises from neural crest tissue and can also secrete catecholamines. The neoplastic counterpart of a glomus tumor in the adrenal gland is the pheochromocytoma, and glomus tumors have been referred to as extra-adrenal pheochromocytoma. Catecholamine secreting glomus tumors can cause arrhythmia, excessive perspiration, headache, nausea and pallor.

Glomus tumors can arise in different regions of the skull base. When confined to the middle ear space, they are termed glomus tympanicum. When arising in the region of the jugular foramen, regardless of their extent, they are termed glomus jugulare. When they arise high in the neck, extending towards the jugular foramen, they are termed glomus vagale. When they arise in the area of the carotid bifurcation, they are called carotid body tumors. Other known sites of glomus tumors include the larynx, orbit, nose, and the aortic arch.

Glomus Jugulare tumors are the most common tumors of the middle ear. These tumors tend to be very vascular and are fed by branches of the external carotid artery. The symptoms of a glomus jugulare tumor include hearing loss with pulsatile ringing in the ear, dizziness, and sometimes ear pain. The patient can have a hearing loss due possibly to blockage of the middle ear, but also there can be a loss of hearing due to nerve injury from the tumor mass. Cranial nerve palsies of the nerves which control swallowing, gagging, shoulder shrugging and tongue movement can all be part of the presentation of glomus jugulare tumors. When the tympanic membrane is examined a red/blue pulsatile mass can often be seen. Symptoms are insidious in onset. Because of the location and the vascular nature of the tumors, a most common complaint is pulsatile tinnitus. It is believed that the tinnitus is secondary to mechanical impingement on the umbo is most cases. Other common symptoms are aural fullness, and (conductive) hearing loss.

Current therapy for a catecholamine secreting glomus tumor is irradiation and/or surgical ablation, preceded by administration of alpha and beta blockers. Treatment for glomus jugulare tumors includes administration of alpha and beta blockers. X-ray therapy can be used to improve symptoms even if the mass persists. It is also possible to embolize the tumor with materials which block its blood supply, however this procedure has associated problems with causing swelling of the tumor which can compress the brain stem and cerebellum as well as releasing the catecholamines from the cells which die when they lose their blood supply. Surgery can be carried out upon small tumors appropriately located. The complications of surgery for a glomus jugulare tumor are persistent leakage of cerebrospinal fluid from the ear and also palsy of one of the cranial nerves controlling face movement, sensation or hearing.

Even though the surgery may be successful glomus jugulare tumors are somewhat problematic because they have a high recurrence rate and may require multiple operations. Surgical ablation carries the risk of morbidity due mainly to iatrogenic cranial nerve deficits and CSF leaks. Lack of cranial nerve preservation is probably the most significant objection to surgical intervention because of the associated morbidity of lower cranial nerve deficits. Radiotherapy also has serious complications, including osteoradionecrosis of the temporal bone, brain necrosis, pituitary-hypothalamic insufficiency, and secondary malignancy. Other postoperative complications include CSF leaks, aspiration syndromes, meningitis, pneumonia and wound infections.

Thus, there are many deficiencies and drawbacks of the current therapies for benign uterine glandular afflictions and uterus cancers and hyperplasic tissues.

What is needed therefore is an effective, non-surgical ablation, non-radiotherapy therapeutic method for treating uterine glandular neoplasms and precancerous hyperplasic uterine tissues.

SUMMARY

The present invention meets this need and provides an effective, non-surgical ablation, non-radiotherapy therapeutic method for treating various precancerous as well as cancerous uterine tissues. Thus, the present invention encompasses methods for treating atypical tissues, such as hyperplasic tissues, cysts and neoplasms (including tumors and cancers) and for preventing the development of, or for causing the regression or remission of, atypical uterine tissues, fibroids and neoplasms. In particular, the present invention encompasses methods for treating uterine glandular disorders, uterine fibroids and neoplasms, both benign and cancerous, as well as for treating hyperplasic and/or hypertonic uterine cells by local administration of a Clostridial toxin to or to the vicinity of the afflicted the uterine tissue.

An embodiment of the present invention is a method for treating a uterine disorder by local administration of between about $10^{-3}$ U/kg and about 2000 U/kg of a Clostridial neurotoxin to a uterine glandular tissue. The Clostridial neurotoxin can be a botulinum toxin. Preferably, the botulinum toxin is administered in an amount of between about $10^{-2}$ U/kg and about 200 U/kg. More preferably, the botulinum toxin is administered in an amount of between about $10^{-1}$ U/kg and about 35 U/kg. The botulinum toxin is selected from the group consisting of botulinum toxins types A, B, C, D, E, F and G and the preferred botulinum toxin is botulinum toxin type A.

The local administration of the botulinum toxin can be carried out by implantation of a botulinum toxin implant into or onto a uterine gland. The uterine gland disorder is selected from the group consisting of precancerous uterine tissue and uterine cancer. Thus, the uterine disorder can be fibroids. The botulinum toxin can be locally administered by direct injection of the botulinum toxin into the uterine glandular tissue.

A more detailed embodiment of the present invention is a method for treating a uterine gland disorder by local administration of between about $10^{-3}$ U/kg and about 2000 U/kg of a botulinum toxin type A to a uterine gland of a human patient, thereby a uterine gland disorder.

My invention also encompasses a method for treating a uterine gland disorder by local administration of a botulinum toxin to a uterine gland or to the vicinity of a precancerous uterine tissue, thereby causing a reduction in the size and/or activity of a hyperplastic, hypertonic or neoplastic uterine gland tissue. This method can reduce the diameter of the hyperplastic, hypertonic or neoplastic uterine gland tissue by between about 20% and about 100%, subsequent to the local administration of the botulinum toxin.

Thus a method for treating a uterine gland disorder as disclosed herein can comprise the step of local administration of a therapeutic amount of a botulinum toxin to a hyperplastic, hypertonic or neoplastic uterine gland tissue, thereby causing a reduction in the diameter of the hyperplastic, hypertonic or neoplastic uterine gland tissue of between is about 20% and about 100%.

Additionally, the present invention encompasses a method for preventing development of a uterine gland neoplasm, the method comprising the step of local administration of a botulinum toxin to a hyperplasic or hypertonic uterine gland tissue, thereby reducing a secretion from the hyperplasic or hypertonic uterine gland tissue and preventing the hyperplasic or hypertonic uterine gland tissue from developing into a neoplasm. In this method the botulinum toxin is administered in an amount of between about $10^{-3}$ U/kg and about 2,000 U/kg and the botulinum toxin is selected from the group consisting of botulinum toxin types A, B, C, D, E, F and G. The botulinum toxin can be locally administered by direct injection of the botulinum toxin into the hyperplasic or hypertonic uterine gland tissue.

To reiterate, a method for preventing development of a uterine gland neoplasm can comprise the step of local administration of a therapeutic amount of a botulinum toxin type A to the precancerous hyperplasic or hypertonic uterine gland tissue of a human patient, thereby preventing development of a uterine gland neoplasm.

Alternately, a method for preventing development of a uterine neoplasm can comprise the step of local administration of between about $10^{-3}$ U/kg and about 2000 U/kg of a botulinum toxin to a hyperplasic tissue, wherein the botulinum toxin reduces a secretion from the hyperplasic tissue by inhibiting a vesicle mediated exocytosis from the precancerous hyperplasic uterine tissue, thereby preventing development of the hyperplasic tissue into a neoplasm. The hyperplasic tissue can comprise a substrate for the botulinum toxin selected from the group of vesicle membrane docking proteins consisting of a 25 kiloDalton synaptosomal associated protein (SNAP-25), synaptobrevin and syntaxin. Furthermore, the botulinum toxin can be administered in an amount of between about 1 U and about 40,000 U, such as between about $10^{-3}$ U/kg and about 35 U/kg, between about $10^{-2}$ U/kg and about 25 U/kg, between about $10^{-2}$ U/kg and about 15 U/kg or between about 1 U/kg and about 10 U/kg. and the local administration of the botulinum toxin is carried out by implantation of a botulinum toxin implant into or onto the body of the uterine tissue.

A detailed embodiment of the present invention is a method for preventing development of a uterine gland carcinoma (that is by preventing the development of a benign [though hyperplasic, metaplasic or atypical] precancerous uterine tissue into a malignant neoplasm or carcinoma), the method comprising the step of local administration of between about $10^{-3}$ U/kg and about 2000 U/kg of a botulinum toxin type A to a hyperplastic, metaplasic or atypical uterine tissue (such as an apocrine cell lined cyst) of a human patient, wherein the uterine tissue comprises a substrate for the botulinum toxin selected from the group of vesicle membrane docking proteins consisting of a 25 kiloDalton synaptosomal associated protein (SNAP-25), synaptobrevin and syntaxin, and wherein the botulinum toxin acts upon the substrate to reduce a secretion from the afflicted uterine tissue.

The present invention includes within its scope a method for treating a neoplasm by local administration of between about $10^{-3}$ U/kg and about 2000 U/kg of a botulinum toxin to the neoplasm, thereby treating the neoplasm by either reducing the size of the neoplasm and/or by reducing a secretion from the uterine neoplasm.

A method according to the present invention can be carried out by direct injection of a botulinum toxin into the body of a neoplasm or by implantation of a botulinum toxin implant into or onto the body of the uterine neoplasm. A method within the scope of the present invention can be practiced to locally administer between about $10^{-3}$ U/kg and about 2000 U/kg of a botulinum toxin to a neoplasm. U/kg means units of a botulinum toxin per kilogram of total patient weight. The botulinum toxin can be one of the botulinum toxin types A, B, $C_1$, D, E, F and G, and is preferably a botulinum toxin type A because of the known clinical efficacy of botulinum toxin type A for a number of indications and because of its ready availability.

Preferably, the botulinum toxin is administered in an amount of between about 1 U and about 40,000 U (total units, not per kg of patient weight). At the higher dose ranges the amount of botulinum toxin administered (i.e. 40,000 units) can be administered in the form of a controlled release delivery system (i.e. an implant), whereby fractional amounts of the botulinum toxin depot (i.e. about 10 units of a botulinum toxin type A or about 500 units of a botulinum toxin type B) are released from the controlled release delivery system over a three to four month period (continuous release delivery system) or is released from the controlled release delivery system in a multiphasic manner in approximate three to four month repeating cycles (pulsatile release delivery system). Suitable controlled release delivery systems to use in the present invention for either the continuous or pulsatile intra or peri-neoplasm release of therapeutic amounts of a botulinum toxin are disclosed in U.S. Pat. Nos. 6,306,423 and 6,312,708.

In a more preferred embodiment of the present invention, the amount of a botulinum toxin type A locally administered to the body of or to a site within the body of the uterine neoplasm according to the present invention can be an amount between about $10^{-3}$ U/kg and about 40 U/kg. Less than about $10^{-3}$ U/kg of a botulinum toxin type A is not expected to result in a significant therapeutic efficacy, while more than about 40 U/kg of a botulinum toxin type A can be expected to result in a toxic or near toxic dose of the toxin. With regard to a botulinum toxin type B, the amount of a botulinum toxin type B locally administered to the neoplasm according to the present invention can be an amount between about $10^{-3}$ U/kg and about 2000 U/kg. Less than about $10^{-3}$ U/kg of a botulinum toxin type B is not expected to result in a significant therapeutic efficacy, while more than about 2000 U/kg of a botulinum toxin type B can be expected to result in a toxic or near toxic dose of the type B toxin. It has been reported that about 2000 units/kg, intramuscular, of a commercially available botulinum toxin type B preparation approaches a primate lethal dose of type B botulinum toxin. Meyer K. E. et al, *A Comparative Systemic Toxicity Study of Neurobloc in Adult and Juvenile Cynomolgus Monkeys*, Mov. Disord 15 (Suppl 2); 54; 2000. With regard to the botulinum toxins types C, D, E, F and G, amounts for injection into a neoplasm can be determined on a patient by patient basis and are not expected to exceed the type B toxin dose range.

In a more preferred embodiment of the present invention, the amount of a type A botulinum toxin administered according to the disclosed methods is between about $10^{-2}$ U/kg and about 25 U/kg. Preferably, the amount of a type B botulinum toxin administered by a continuous release system during a given period is between about $10^{-2}$ U/kg and about 1000 U/kg, since it has been reported that less than about 1000 U/kg of type B botulinum toxin can be intramuscularly administered to a primate without systemic effect. Ibid. More preferably, the type A botulinum toxin is administered in an amount of between about $10^{-1}$ U/kg and about 15 U/kg. Most preferably, the type A botulinum toxin is administered in an amount of between about 1 U/kg and about 10 U/kg. In many instances, an intra-neoplastic administration of from about 1 units to less than about 100 units of a botulinum toxin type A, can provide effective and long lasting therapeutic relief, as set forth herein. More preferably, from about 5 units to about 75 units of a botulinum toxin, such as a botulinum toxin type A, can be used and most preferably, from about 5 units to about 50 units of a botulinum toxin type A, can be locally administered into a target neoplasm tissue with efficacious results. In a particularly preferred embodiment of the present invention from about 1 unit to about 50 units of a botulinum toxin, such as botulinum toxin type A, can be locally administered to a neoplasm target tissue with therapeutically effective results, as described herein.

A detailed method within the scope of the present invention can be carried out by local administration of between about $10^{-3}$ U/kg and about 2000 U/kg of a botulinum toxin type A to a neoplasm of a human patient, thereby reducing a secretion from the uterine neoplasm.

"Local administration" means direct injection of the neurotoxin into or to the local area of the target uterine tissue. Systemic routes of administration, such as oral and intravenous routes of administration, are excluded from the scope of the present invention.

The botulinum toxin can be a modified botulinum toxin, that is the botulinum toxin can have at least one of its amino acids deleted, modified or replaced, as compared to a native botulinum toxin. Thus, the botulinum toxin can be a recombinant produced botulinum toxin or a derivative or fragment thereof.

DRAWINGS

DESCRIPTION

Figure 1:
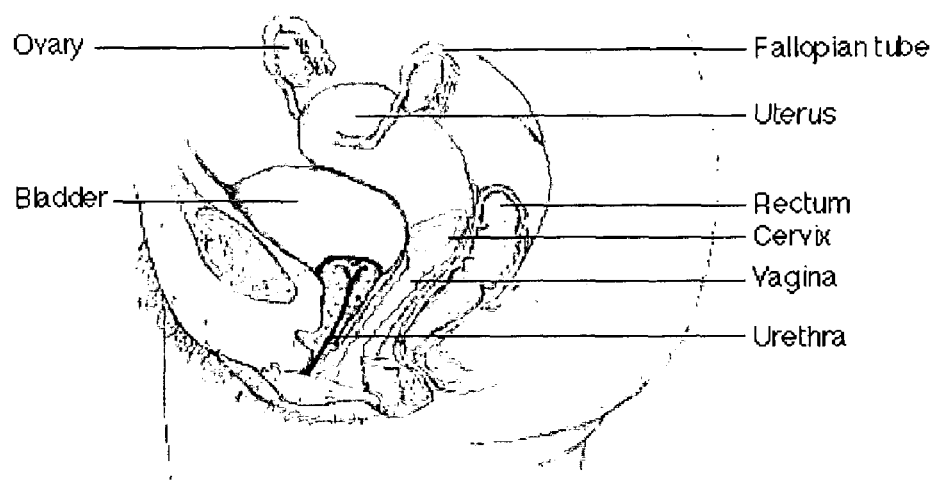
FIG. 1 is a diagrammatic representation in partial cross section of the location of the uterus of a human female in relation to adjacent organs.

The present invention is based upon the discovery that hyperplasic, hypertonic, cystic and/or neoplastic uterine tissues can be treated with a Clostridial toxin to thereby reduce or eliminate the hyperplasia, hypertonia, cystic and/or neoplastic condition. The tissue treated can be benign or malignant and hyperplasia includes a hypertonic condition. The present invention is therefore applicable to the treatment of conditions which include uterine cancer, and fibroids, as well as to hyperplasic, metaplasic, atypia and dysplasic precancerous uterine tissues.

Additionally, excessively secreting uterine cells (hyperplasic or hypertonic) wherein the secretory activity is controlled or influenced by one or more of the botulinum toxin substrates can be treated by a method within the scope of the present invention so as to prevent the development of the hyperplasic or hypertonic uterine secretory tissue into a neoplasm. In the target tissue the proteolytic light chain of the botulinum toxin is internalized.

Without wishing to be bound by theory, a physiological mechanism for the efficacy of the present invention can be proposed. Thus, it is known that uterine muscle tissue is influenced by cholinergic neurons. See e.g. Morris, J., et al, *Botulinum neurotoxin A attenuates release of norepinephrine but not NPY from vasoconstrictor neurons*, Am J Physiol Heart Circ Physiol 2002 December; 283 (6). Additionally, it is known that cholinergic innervation of uterine glandular tissues affects the secretory activity of such cells. See e.g. Hammarstron M., et al., *Does nitric oxide act as a cellular messenger in muscarinic endometrial secretion in the guinea-pig?*, Acta Physiol Scand 2002 April; 174(4):311-5. Thus, uterine secretory cells receive at least a sympathetic cholinergic secremotor innervation. Hence it can be postulated that local administration of a botulinum toxin to a uterine glandular tissue can act to reduce secretory activity by such glandular cells (either by inhibition of secretion promoting, cholinergic innervation to the cells or by a direct effect upon of the toxin upon uterine glandular cells wherein toxin substrates SNAP-25 or VAMP promote membrane docking or fusion of secretory vesicles), thereby reducing a uterine glandular hyperplasia, which leads to a remission of fibroid development and furthermore inhibits progression or development of a hyperplasic (i.e. precancerous) uterine glandular cell into a uterine cancer, tumor or neoplasm.

In a preferred embodiment the present invention is a method for treat uterine disease, such as precancerous uterine tissues. Although the present invention is not limited to any particular mechanism, it can be hypothesized that local administration of a Clostridial toxin (such as a botulinum toxin) to an afflicted tissue, such as a uterine fibroid, results in treatment of the i.e. fibroid (i.e. reduction of [or total elimination of] size the fibroid, and/or of the uterine cell hyperplasia) due to either an inhibitory effect of the toxin upon stimulatory cholinergic fibers which innervate the uterine cells or a direct effect of the toxin upon the fibroid upon internalization of the toxin (or at least of the toxin light chain) by fibroid cells.

Thus a preferred embodiment of the present invention is a method for treating a precancerous uterine disorder, such as uterine fibroids, ad enosis, papillomas, and fibroadenomas (hyperplasia lobules). By precancerous it is meant that the afflicted uterine tissue is not-malignant (i.e. is not cancerous), although it can be hyperplasic, hypertrophic or metaplasic, and that the presence of the precancerous tissue increases the risk to the patient of development of a uterine cancer.

Thus, cholinergically innervated uterine target tissues can be treated by local administration of a Clostridial toxin, such as a botulinum toxin. By local administration it is meant that the neurotoxin is administered directly into, or to the vicinity of the target tissue (i.e. a precancerous uterine tissue) or local tissue area to be treated. Local administration includes injection of the neurotoxin directly into the afflicted tissue. Noncancerous (benign), precancerous, cancerous (malignant) hyperplasic and/or hypertonic secretory tissues can be treated by a method within the scope of the present invention. Nodular or diffuse hyperplasia which precedes tumor development can be treated by the present method.

I have discovered that a particular neurotoxin, botulinum toxin, can be used with dramatic ameliorative effect to treat a variety of precancerous uterine tissues, thereby significantly superseding current surgical, chemotherapy and radiotherapy therapeutic methods. Significantly, a single local administration of the botulinum toxin can be used to successfully treat a uterine disease.

Figure 2:
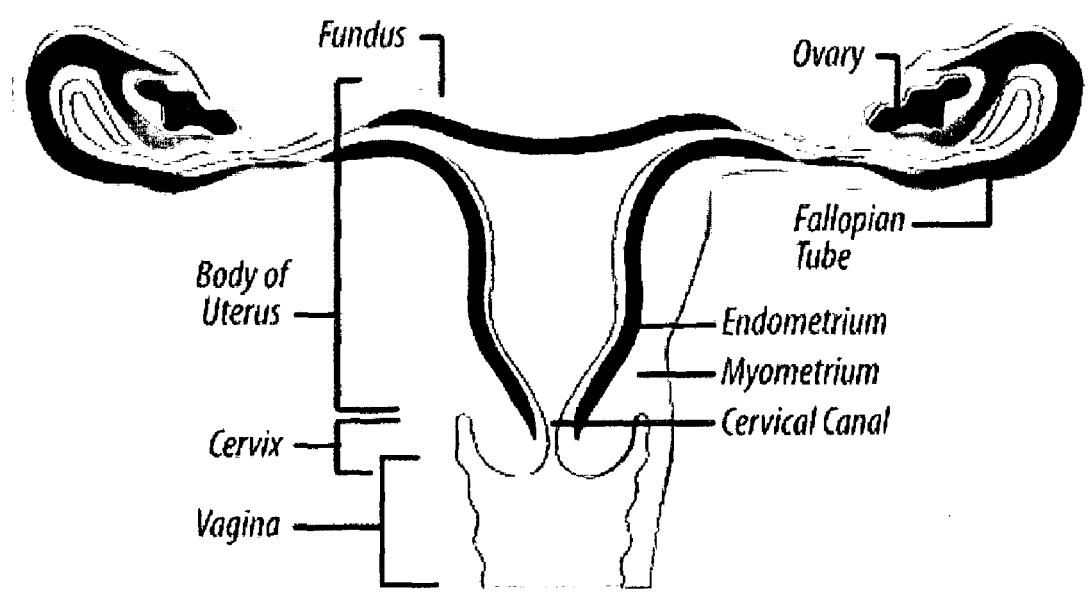
FIG. 2 is diagrammatic cross sectional representation of the uterus of FIG. 1.
Figure 3:
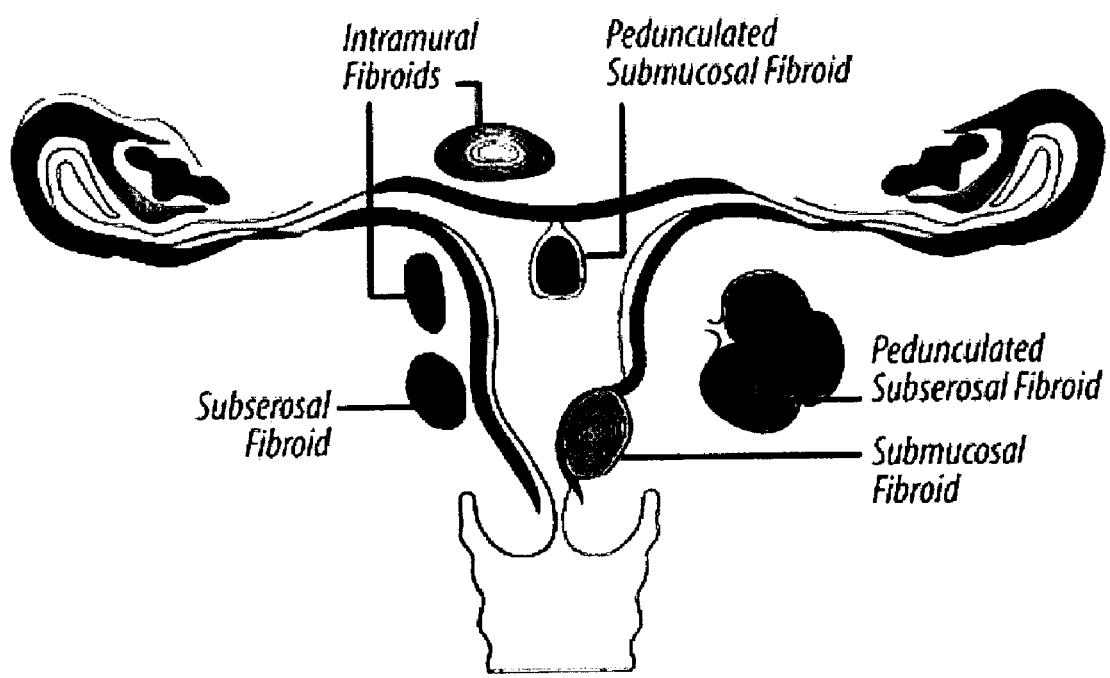
FIG. 3 is diagrammatic cross sectional representation of the uterus of FIG. 2 showing location of different types of uterine fibroids.

As shown by FIG. 1, the uterus is situated in proximity to the bladder and the intestine. FIG. 2 shows that the uterus comprises a fundus, body, cervix, cervical canal, endometrium and myometrium. Various types of fibroids are possible, including intramural, pedunculated submucosal, pedunculated subserosal, submucosal, and subserosal fibroids and typical uterine location are shown by FIG. 3.

The route of administration and amount of botulinum toxin administered can vary widely according to the particular uterine gland disorder being treated and various patient variables including size, weight, age, disease severity and responsiveness to therapy. Method for determining the appropriate route of administration and dosage are generally determined on a case by case basis by the attending physician. Such determinations are routine to one of ordinary skill in the art (see for example, *Harrison's Principles of Internal Medicine* (1997), edited by Anthony Fauci et al., 14th edition, published by McGraw Hill). Treatment is carried out so as to substantially avoiding entry of the toxin into the systemic circulation (i.e. by use of subcutaneous or intramuscular injection as opposed to intravenous administration).

The specific dosage appropriate for administration is readily determined by one of ordinary skill in the art according to the factors discussed above. The dosage can also depend upon the size of the tumor to be treated or denervated, and the commercial preparation of the toxin. Additionally, the estimates for appropriate dosages in humans can be extrapolated from determinations of the amounts of botulinum required for effective denervation of other non-neoplastic tissues. Thus, the amount of botulinum A to be injected is proportional to the mass and level of activity of the uterine tissue to be treated. Generally, between about 0.01 and 2000 units per kg of patient weight of a botulinum toxin, such as botulinum toxin type A, can be administered to effectively accomplish a toxin induced target tissue atrophy upon administration of the neurotoxin at or to the vicinity of the uterine target tissue. Less than about 0.01 U/kg of a botulinum toxin does not have a significant therapeutic effect while more than about 2000 U/kg or 35 U/kg of a botulinum toxin B or A, respectively, approaches a toxic dose of the specified botulinum toxin. Careful placement of the injection needle and a low volume of neurotoxin used prevents significant amounts of botulinum toxin from appearing systemically. A more preferred dose range is from about 0.01 U/kg to about 25 U/kg of a botulinum toxin, such as that formulated as BOTOX®. The actual amount of U/kg of a botulinum toxin to be administered depends upon factors such as the extent (mass) and level of activity of the i.e. hyperplasic uterine tissue to be treated and the administration route chosen. Botulinum toxin type A is a preferred botulinum toxin serotype for use in the methods of the present invention.

The main site of action of botulinum toxin is the neuromuscular junction where the toxin binds rapidly and prevents the release of acetylcholine. Thus, while it is known that the botulinum toxins have a known binding affinity for cholinergic, pre-synaptic, peripheral motor neurons, I have discovered that the botulinum toxins can also bind to and translocate into a variety of precancerous uterine tissues, where the toxin then acts, in the known manner, as an endoprotease upon its respective secretory vessel-membrane docking protein. Because of the lower affinity of the botulinum toxins for certain uterine tissues, the toxin can preferably injected into secretory or glandular tissues to provide a high local concentration of the toxin. Thus, the present invention is applicable to the treatment of precancerous uterine tissues which may have with little or no cholinergic innervation.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known use for the treatment of skeletal and smooth muscle disorders when locally administered by intramuscular injection.

A route for administration of a neurotoxin according to the present disclosed invention for treating a precancerous uterine tissue can be selected based upon criteria such as the solubility characteristics of the neurotoxin toxin chosen as well as the amount of the neurotoxin to be administered. The amount of the neurotoxin administered can vary widely according to the particular disorder being treated, its severity and other various patient variables including size, weight, age, and responsiveness to therapy. For example, the extent of the precancerous uterine tissue influenced is believed to be proportional to the volume of neurotoxin injected, while the quantity of the denervation is, for most dose ranges, believed to be proportional to the concentration of neurotoxin injected. Methods for determining the appropriate route of administration and dosage are generally determined on a case by case basis by the attending physician. Such determinations are routine to one of ordinary skill in the art (see for example, Harrison's Principles of Internal Medicine (1997), edited by Anthony Fauci et al., 14th edition, published by McGraw Hill).

The present invention includes within its scope the use of any neurotoxin which has a long duration therapeutic effect when locally applied to a precancerous uterine tissue of a patient. For example, neurotoxins made by any of the species of the toxin producing *Clostridium* bacteria, such as

*Clostridium botulinum, Clostridium butyricum,* and *Clostridium beratti* can be used or adapted for use in the methods of the present invention. Additionally, all of the botulinum serotypes A, B, C, D, E, F and G can be advantageously used in the practice of the present invention, although type A is the most preferred serotype, as explained above. Practice of the present invention can provide target tissue atrophy and remission for 27 months or longer in humans.

It is known that catecholamine release from permeabilized adrenal medulla cells can be inhibited by a botulinum toxin. Additionally, it is known that release of insulin from permeabilized (as by electroporation) insulin secreting cells can be inhibited by a botulinum toxin. When in vitro, the cell membranes of these non-nerve cells can be permeabilized to assist introduction of a botulinum toxin into the cell's cytosol due to the lack of cell surface receptors for a botulinum toxin. Thus, botulinum toxin type B apparently inhibits insulin secretion by cleaving synaptobrevin present in the insulin secreting cell line HIT-15. Boyd R. S., et al *The Effect of Botulinum Neurotoxin-B On Insulin Release From a Beta Cell*, Mov Disord 10(3):376 (1995). It is the inventor's contention that a botulinum toxin can block the release of any vesicle mediated exocytosis from any secretory (i.e. neuronal, glandular, secretory, chromaffin) cell type, as long as the light chain of the botulinum toxin is translocated into the intracellular medium. For example, the intracellular protein SNAP-25 is widely distributed in both neuronal and non-neuronal secretory cells and botulinum toxin type A is an endopeptidase for which the specific substrate is SNAP-25. Thus, while cholinergic neurons have a high affinity acceptor for the botulinum and tetanus toxins (and are therefore more sensitive than other neurons and other cells to the inhibition of vesicle mediated exocytosis of secretory compounds), as the toxin concentration is raised, non-cholinergic sympathetic neurons, chromaffin cells and other cell types can take up a botulinum toxin and show reduced exocytosis.

Hence, by practice of the present disclosed invention, non-cholinergic nerve fibers as well as non or poorly innervated secretory uterine neoplasms can be treated by use of an appropriately higher concentration of a botulinum toxin to bring about therapeutic atrophy of secretory uterine neoplasms.

Furthermore, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assesses using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

As set forth above, I have discovered that a surprisingly effective and long lasting therapeutic effect can be achieved by local administration of a neurotoxin to a precancerous uterine tissue of a human patient. In its most preferred embodiment, the present invention is practiced by direct injection into the target tissue or to the local area of the target tissue of botulinum toxin type A. It has been reported that at the neuroglandular junction, the chemical denervation effect of a botulinum toxin, such as botulinum toxin type A, has a considerably longer duration of action, i.e. 27 months vs. 3 months.

The present invention does include within its scope: (a) neurotoxin complex as well as pure neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, and includes neurotoxins with one or more attached targeting moieties for chromaffin and neoplasm cells types.

Botulinum toxins for use according to the present invention can be stored in lyophilized or vacuum dried form in containers under vacuum pressure. Prior to lyophilization the botulinum toxin can be combined with pharmaceutically acceptable excipients, stabilizers and/or carriers, such as albumin. The lyophilized or vacuum dried material can be reconstituted with saline or water.

In each of the following examples, the specific amount of a botulinum toxin administered depends upon a variety of factors to be weighed and considered within the discretion of the attending physician and in each of the examples insignificant amounts of botulinum toxin enter appear systemically with no significant side effects. Units of botulinum toxin injected per kilogram (U/kg) below are per kg of total patient weight. For example, 3 U/kg for a 70 kg patient calls for an injection of 210 units of the botulinum toxin.

EXAMPLES

The following examples provide those of ordinary skill in the art with specific preferred methods within the scope of the present invention for carrying out the present invention and are not intended to limit the scope of what the inventors regards as their invention.

In each of the following examples, the specific amount of a botulinum toxin (such as BOTOX®) administered depends upon a variety of factors In to be weighed and considered within the discretion of the attending physician.

Example One

Use of a Botulinum Toxin to Treat Fibroids

A 46 year old female presents with uterine fibroids. Ultrasound and imaging investigation reveals multiple fibroids. Histological examination reveals the present of endometrial atypia (both hyperplasia and metaplasia) and the patient is therefore determined to be at risk for development of carcinoma. Local administration (injection) of from 10 unit to 100 units of a botulinum toxin type A, such as BOTOX®, into the fibroid mass at several locations is carried out. Within 28 days thereafter the fibroids have substantially regressed (fibroid diameter reduced by at least 80%) and remains so for the ensuing 2 to 24 months. Alternately, a botulinum toxin type B, C, D, E, F or G can be administered, with the dosing amount adjusted to reflect the differing potency as compared to the type A toxin. Thus, for example, since botulinum toxin type B is known to be about 50 times less potent that botulinum toxin type A, from 500 to 5000 unit of type B toxin is local administered. Alternately, for extended therapeutic effect, a controlled release implant can be inserted subcutaneously and/or a suspension of botulinum containing microspheres can be injected, as set forth in U.S. Pat. Nos. 6,306,423 and 6,312,708.

Example 2

Treatment of Uterine Hypertonic or Hyperplasic Tissues with a Botulinum Toxin

A 64 year old woman is diagnosed with precancerous, hyperplasic uterine tissues. Local administration (injection) of from 10 unit to 100 units of a botulinum toxin type A, such as BOTOX® into the hyperplasic tissues is carried out. Within 28 days thereafter the hyperplasia have substantially regressed and remains so for the ensuing 2 to 24 months. Alternately, a botulinum toxin type B, C, D, E, F or G can be administered, with the dosing amount adjusted to reflect the differing potency as compared to the type A toxin. Thus, for example, since botulinum toxin type B is known to be about 50 times less potent that botulinum toxin type A, from 500 to 5000 unit of type B toxin is local administered. Alternately, for extended therapeutic effect, a controlled release implant can be inserted subcutaneously and/or a suspension of botulinum containing microspheres can be injected, as set forth in U.S. Pat. Nos. 6,306,423 and 6,312,708. The same local administration method can be carried out to treat a uterine metastatic lesion, as wells as preoperative prior to surgical removal of a hyperplasic, or cancerous uterine tissue.

Methods according to the invention disclosed herein has many advantages, including the following:
(1) the invention renders unnecessary surgery for effective treatment of diverse uterine diseases, including hyperplasic, hypertonic and metaplasic uterine tissues.
(2) systemic drug effects can be avoided by direct local application of a neurotoxin according to the present invention
(3) the ameliorative effects of the present invention can persists for two years or longer from a single local administration of a neurotoxin as set forth herein.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local otic administration methods wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type E. Alternately, a combination of any two or more of the botulinum serotypes A-G an be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect.

My invention also includes within its scope the use of a neurotoxin, such as a botulinum toxin, in the preparation of a medicament for the treatment of a precancerous uterine tissue by local administration of the neurotoxin. All references, articles, publications and patents cited above are incorporated herein by reference in their entireties.

Accordingly, the spirit and scope of the following claims should not be limited to the descriptions of the preferred embodiments set forth above.

I claim:

1. A method for treating a uterine fibroid, the method comprising the step of local administration of between about $10^{-3}$ U/kg and about 2000 U/kg of a native, unmodified botulinum toxin that is not conjugated to a targeting moiety, to the uterine fibroid, thereby treating the uterine fibroid.

2. The method of claim 1, wherein the botulinum toxin is selected from the group consisting of botulinum toxin types A, B, C, D, E, F and G.

3. The method of claim 1, wherein the botulinum toxin is botulinum toxin is botulinum toxin type A.

4. The method of claim 1, wherein the botulinum toxin is administered in an amount of between about $10^{-2}$ U/kg and about 200 U/kg.

5. The method of claim 1, wherein the botulinum toxin is administered in an amount of between about $10^{-1}$ U/kg and about 35 U/kg.

6. The method of claim 1, wherein treating the uterine fibroid further reduces the distortion of the endometrial cavity.

7. The method of claim 1, wherein treating the uterine fibroid further reduces the frequency of miscarriages.

8. The method of claim 1, wherein treating the uterine fibroid further prevents the fibroid from becoming malignant.

* * * * *

UNITED STATES PATENT AND TRADEMARK OFFICE
CERTIFICATE OF CORRECTION

| | |
|---|---|
| PATENT NO. | : 8,071,550 B2 |
| APPLICATION NO. | : 10/379157 |
| DATED | : December 6, 2011 |
| INVENTOR(S) | : Schiffman |

It is certified that error appears in the above-identified patent and that said Letters Patent is hereby corrected as shown below:

On first page, field (56), under "OTHER PUBLICATIONS", in column 2, line 34, Delete "Gistof" and insert -- Gistol --, therefor.

On first page, field (56), under "OTHER PUBLICATIONS", in column 2, line 36, Delete "Blasl," and insert -- Blasi, --, therefor.

On first page, field (56), under "OTHER PUBLICATIONS", in column 2, line 36, Delete "Botuligum" and insert -- Botulinum --, therefor.

On first page, field (56), under "OTHER PUBLICATIONS", in column 2, line 43, Delete "Organophosphorous" and insert -- Organophosphorus --, therefor.

On first page, field (56), under "OTHER PUBLICATIONS", in column 2, line 44, Delete "Acetycholinesterase" and insert -- Acetylcholinesterase --, therefor.

On page 2, under "OTHER PUBLICATIONS", in column 1, line 22, Delete "Syntaxinl;" and insert -- Syntaxin1; --, therefor.

On page 2, under "OTHER PUBLICATIONS", in column 1, line 33, Delete "insul" and insert -- insulin --, therefor.

On page 2, under "OTHER PUBLICATIONS", in column 1, line 37, Delete "assocated" and insert -- associated --, therefor.

On page 2, under "OTHER PUBLICATIONS", in column 1, line 38, Delete "1996;236(3)" and insert -- 1996; 236(3) --, therefor.

On page 2, under "OTHER PUBLICATIONS", in column 2, line 25, Delete "neoplasis," and insert -- neoplasia, --, therefor.

In column 1, line 33-59, Delete "It is known that hyperplasic uterine tissues can, if not treated, develop into cancerous tissue. See e.g. Sivridis E. et al., Prognostic aspects on endometrial hyperplasia and neoplasia, Signed and Sealed this
Twenty-eighth Day of February, 2012

David J. Kappos
*Director of the United States Patent and Trademark Office*

Virchows Arch 2001 August; 439(2): 118-26. Additionally it is known that: different hyperplasia, metaplasic or atypical breast tissues can develop into cancers (see e.g. Ellis I. O., et al, Tumors of the Breast, chapter 16 (pages 865-930) of "Diagnostic Histopathology of Tumors", volume 1, edited by Fletcher C. D. M., second edition, Churchill Livingstone (2000), discussed further infra, as well as Fabian C. J. et al Beyond tamoxifen new endpoints for breast cancer chemoprevention, new drugs for breast cancer prevention. Ann NY Acad Sci 2001 December; 952:44-59); hyperplasic intestinal tissues, such as polyps can transform into carcinomas (see e.g. Der, R. et al Gastric Neoplasms, chapter 5 (pages 105-144) of Chandraspma, P., "Gastrointestinal Pathology", Appleton & Lange (1999), in particular pages 106-107; oral and oropharyngeal epithelial hyperplasia indicates a precancerous lesion. Sunaga H., et al. Expression of granulocyte colony-stimulating factor receptor and platelet-derived endothelial cell growth factor in oral and oropharyngeal precancerous lesions. Anticancer Res 2001 July-August; 21 (4B):2901-6, and; kidney and prostate cell hyperplasia has been documented as a factor leading to development of cancerous cells. Van Poppel, H., et al., Precancerous lesions in the kidney Scand J Urol Nephrol Suppl 2000; (205): 136-65."

and insert -- It is known that hyperplasic uterine tissues can, if not treated, develop into cancerous tissue. See e.g. Sivridis E. et al., Prognostic aspects on endometrial hyperplasia and neoplasia, Virchows Arch 2001 August; 439(2): 118-26. Additionally it is known that: different hyperplasia, metaplasic or atypical breast tissues can develop into cancers (see e.g. Ellis I. O., et al, Tumors of the Breast, chapter 16 (pages 865-930) of "Diagnostic Histopathology of Tumors", volume 1, edited by Fletcher C. D. M., second edition, Churchill Livingstone (2000), discussed further infra, as well as Fabian C. J. et al Beyond tamoxifen new endpoints for breast cancer chemoprevention, new drugs for breast cancer prevention. Ann NY Acad Sci 2001 December; 952:44-59); hyperplasic intestinal tissues, such as polyps can transform into carcinomas (see e.g. Der, R. et al Gastric Neoplasms, chapter 5 (pages 105-144) of Chandraspma, P., "Gastrointestinal Pathology", Appleton & Lange (1999), in particular pages 106-107); oral and oropharyngeal epithelial hyperplasia indicates a precancerous lesion. Sunaga H., et al. Expression of granulocyte colony-stimulating factor receptor and platelet-derived endothelial cell growth factor in oral and oropharyngeal precancerous lesions. Anticancer Res 2001 July-August; 21 (4B):2901-6, and; kidney and prostate cell hyperplasia has been documented as a factor leading to development of cancerous cells. Van Poppel, H., et al., Precancerous lesions in the kidney Scand J Urol Nephrol Suppl 2000; (205): 136-65. --, therefor.

CERTIFICATE OF CORRECTION (continued)
U.S. Pat. No. 8,071,550 B2

In column 2, line 19, Delete "rapidly" and insert -- rapidly) --, therefor.

In column 4, line 34, After "acetylcholine." delete "[1]Available from Allergan, Inc., of Irvine, Calif. under the tradename BOTOX®.".

In column 4, line 42, After "A" insert -- . --.

In column 5, line 10, Delete "hemaglutinin" and insert -- hemagglutinin --, therefor.

In column 5, line 11, Delete "nonhemaglutinin" and insert -- nonhemagglutinin --, therefor.

In column 6, line 20, Delete "sublimus:" and insert -- sublimis: --, therefor.

In column 7, line 33, Delete "(see" and insert -- see --, therefor.

In column 7, line 61, Delete "norepinephine." and insert -- norepinephrine. --, therefor.

In column 9, line 36, Delete "1995;" and insert -- 1995); --, therefor.

In column 9, line 49, Delete "1997;" and insert -- 1997); --, therefor.

In column 9, line 50, Delete "(Graff," and insert -- Graff, --, therefor.

In column 10, line 5, Delete "systems.");" and insert -- systems"); --, therefor.

In column 10, line 9-10, Delete "mammososmatotroph" and insert -- mammosomatotroph --, therefor.

In column 10, line 22, Delete "(Shukla" and insert -- Shukla --, therefor.

In column 10, line 30, Delete "(Grosse" and insert -- Grosse --, therefor.

In column 10, line 36, Delete "cells"." and insert -- cells"). --, therefor.

In column 10, line 46, Delete "(Dorosevichi" and insert -- (Dorosevich --, therefor.

In column 10, line 59, Delete "organophosphorous" and insert -- organophosphorus --, therefor.

In column 12, line 29, Delete "ayer's" and insert -- layer's --, therefor.

In column 12, line 37, Delete "tonsils)." and insert -- tonsils. --, therefor.

In column 12, line 50, Delete "as" and insert -- at --, therefor.

In column 15, line 43, After "between" delete "is".

In column 16, line 15, Delete "U/kg." and insert -- U/kg --, therefor.

In column 17, line 21-30, Delete "toxin. It has been reported that about 2000 units/kg, intramuscular, of a commercially available botulinum toxin type B preparation approaches a primate lethal dose of type B botulinum toxin. Meyer K. E. et al, A Comparative Systemic Toxicity Study of Neurobloc in Adult and Juvenile Cynomolgus Monkeys, Mov. Disord 15 (Suppl 2); 54; 2000. With regard to the botulinum toxins types C, D, E, F and G, amounts for injection into a neoplasm can be determined on a patient by patient basis and are not expected to exceed the type B toxin dose range." and insert the same after "type B" in column 17, Line 20, as a continuation of the same paragraph.

CERTIFICATE OF CORRECTION (continued)
U.S. Pat. No. 8,071,550 B2

In column 18, line 4-6, Delete "compared to a native botulinum toxin. Thus, the botulinum toxin can be a recombinant produced botulinum toxin or a derivative or fragment thereof." and insert the same after "replaced, as" in column 18, Line 3, as a continuation of the same paragraph.

In column 18, line 29, Delete "dysplasic" and insert -- dysplasia --, therefor.

In column 18, line 56, After "effect" delete "upon".

In column 22, line 43, After "factors" delete "In".

In column 23, line 27, Delete "wells" and insert -- well --, therefor.

In column 23, line 36, After "invention" insert -- . --.

In column 24, line 5, Delete "an" and insert -- can --, therefor.

In column 24, line 31, In Claim 3, after "the" delete "botulinum toxin is".